United States Patent
Li et al.

(10) Patent No.: US 11,945,775 B2
(45) Date of Patent: Apr. 2, 2024

(54) STABLE DISPERSANT AND APPLICATION THEREOF IN PREPARING COPOLYMER POLYOLS

(71) Applicant: WANHUA CHEMICAL GROUP CO., LTD., Shandong (CN)

(72) Inventors: Fuguo Li, Shandong (CN); Yang Liu, Shandong (CN); Changxun Ju, Shandong (CN); Bin Liu, Shandong (CN); Chengqun Qin, Shandong (CN); Xunkun Wu, Shandong (CN); Jing Li, Shandong (CN); Bing Zheng, Shandong (CN); Lunpeng Wang, Shandong (CN)

(73) Assignee: WANHUA CHEMICAL GROUP CO., LTD., Shandong (CN)

( * ) Notice: Subject to any disclaimer, the term of this patent is extended or adjusted under 35 U.S.C. 154(b) by 396 days.

(21) Appl. No.: 17/294,102

(22) PCT Filed: Dec. 26, 2018

(86) PCT No.: PCT/CN2018/123934
§ 371 (c)(1),
(2) Date: May 14, 2021

(87) PCT Pub. No.: WO2020/124645
PCT Pub. Date: Jun. 25, 2020

(65) Prior Publication Data
US 2022/0017448 A1 Jan. 20, 2022

(30) Foreign Application Priority Data
Dec. 21, 2018 (CN) .......................... 201811569144.3

(51) Int. Cl.
C08G 18/08 (2006.01)
C07C 67/26 (2006.01)
C08G 101/00 (2006.01)

(52) U.S. Cl.
CPC .......... *C07C 67/26* (2013.01); *C08G 18/0876* (2013.01); *C08G 18/14* (2013.01); *C08G 2101/00* (2013.01)

(58) Field of Classification Search
CPC ...... C07C 67/26; C08F 212/10; C08F 220/44; C08F 283/06; C08G 18/0876; C08G 18/14; C08G 18/18; C08G 18/244; C08G 18/302; C08G 18/3275; C08G 18/4837; C08G 18/632; C08G 65/14; C08G 65/2615; C08G 65/332; C08G 65/3322; C08G 65/3324; C08G 2101/00; C08G 2110/0008; C08G 2110/0083; C09J 133/066
See application file for complete search history.

(56) References Cited

U.S. PATENT DOCUMENTS

| | | | |
|---|---|---|---|
| 3,652,639 A | 3/1972 | Pizzini et al. | |
| 3,823,201 A | 7/1974 | Pizzini et al. | |
| 5,196,476 A | 3/1993 | Simroth | |
| 5,834,118 A * | 11/1998 | Ranby ............... | C08G 63/20 528/297 |
| 2002/0161138 A1 | 10/2002 | Honjo et al. | |

FOREIGN PATENT DOCUMENTS

| | | |
|---|---|---|
| CN | 1354764 A | 6/2002 |
| CN | 101311203 A | 11/2008 |
| CN | 103068866 A | 4/2013 |
| CN | 106255711 A | 12/2016 |
| CN | 108559033 A | 9/2018 |
| EP | 0461800 A1 | 12/1991 |
| EP | 0786480 A1 | 7/1997 |
| EP | 1942122 A2 | 7/2008 |
| WO | 9940144 A1 | 8/1999 |
| WO | 02085964 A2 | 10/2002 |
| WO | 2005015309 A2 | 2/2005 |
| WO | 2008005708 A1 | 1/2008 |
| WO | 2018019708 A1 | 2/2018 |

OTHER PUBLICATIONS

European Search Report dated Aug. 12, 2022 in corresponding patent application EP 18943439.2-1102.
Office Action issued in corresponding Chinese Patent Application No. 201811569144.3 dated Nov. 6, 2020, with English translation.
International Search Report issued in PCT/CN2018/123934 dated May 28, 2019.

* cited by examiner

Primary Examiner — John M Cooney
(74) Attorney, Agent, or Firm — Norton Rose Fulbright US LLP; James R. Crawford

(57) ABSTRACT

A stable dispersant and an application thereof in preparing copolymer polyols, the preparation method for the stable dispersant including the steps of 1) contacting a polyol with a dianhydride compound for reaction so as to prepare an adduct; 2) performing a ring-opening addition reaction on the adduct obtained in step 1) and an epoxy compound to prepare a stable dispersant; the dianhydride compound does not contain a double bond that may copolymerize with an olefinically unsaturated monomer, while the epoxy compound contains a double bond that may copolymerize with an olefinically unsaturated monomer, the polyol is a polyester polyol and/or a polyether polyol, preferably being a polyether polyol. The stable dispersant obtained by means of the described preparation method has a multi-active site anchoring function, and is applied to the synthesis of copolymer polyols to obtain copolymer polyols having relatively uniform particle size.

7 Claims, 3 Drawing Sheets

STABLE DISPERSANT AND APPLICATION THEREOF IN PREPARING COPOLYMER POLYOLS

CROSS REFERENCE TO RELATED APPLICATIONS

This application is a national phase under 35 U.S.C. § 371 of International Application No. PCT/CN2018/123934 filed Dec. 26, 2018, which claims the benefit of priority to Chinese Application No. 201811569144.3 filed on Dec. 21, 2018, the entire contents of each of which are hereby incorporated by reference in their entirety.

TECHNICAL FIELD

The present disclosure relates to the technical field of the preparation of copolymer polyols and specifically, to the synthesis of a new stable dispersant and an application thereof in preparing copolymer polyols.

BACKGROUND

Copolymer polyols are often used in the manufacture of polyurethane foams to improve bearing capacity and other properties of polyurethane foams. The copolymer polyols are dispersions of polymers in polyols. Commonly used types of copolymer polyols are vinyl polymer particle polyols (styrene-acrylonitrile dispersions), polyurea particle dispersions (PHD polyols), and polyisocyanate addition polymers (PIPA polyols, dispersions of polyurethane-polyurea particles). Currently, styrene/acrylonitrile copolymers are widely commercialized as dispersions in polyols (referred to as copolymer polyols or polymer dispersions, abbreviated as POP).

Their stability is mostly achieved by the stabilizing effect of grafted or addition products formed between the polymers of unsaturated compounds and the polyol molecules. The stabilizers used in the existing art are all single-active site ones, as shown in FIG. 6.

The common method is to introduce a small amount of unsaturation degree into the polyol. As disclosed in U.S. Pat. Nos. 3,652,639 and 3,823,201, stable dispersants with specific reactive unsaturation degree are used for the preparation of copolymer polyols, but the solid contents of the prepared copolymer polyols are low. The later patents U.S. Pat. No. 5,196,476 and EP0786480 disclose the method of preparing POP by the preformed stabilizer method. In this method, a free radical polymerization initiator, a stable dispersant, and an ethylenically unsaturated monomer react to prepare a preformed stabilizer, and then, the preformed stabilizer continues to polymerize with the ethylenically unsaturated monomer in the presence of polyether to prepare POP. This method has the defects of the usage of a large number of stable dispersants and high viscosity.

SUMMARY

In view of the above, the present disclosure provides a new stable dispersant. The stable dispersant is particularly suitable for the application in preparing copolymer polyols. The stable dispersant also has more active sites and relatively low viscosity, and can be used to prepare copolymer polyols with relatively homogeneous particle size.

To achieve the above objective, the present disclosure adopts the technical solutions described below.

One aspect of the present disclosure provides a preparation method for a stable dispersant. The preparation method includes: 1) contacting a polyol with a dianhydride compound for reaction to prepare an adduct, wherein the reaction is specifically an anhydride ring-opening reaction; and 2) performing a ring-opening addition reaction on the adduct obtained in step 1) and an epoxy compound to prepare a stable dispersant;

wherein the dianhydride compound does not contain a double bond that may copolymerize with an olefinically unsaturated monomer while the epoxy compound contains a double bond that may copolymerize with an olefinically unsaturated monomer, and the polyol is a polyester polyol and/or a polyether polyol, preferably a polyether polyol. The stable dispersant obtained by means of the above preparation method has a multi-active site anchoring function and is applied to the synthesis of copolymer polyols to obtain copolymer polyols with relatively homogeneous particle size. The stable dispersant also has great stable dispersity.

In some preferred embodiments, the dianhydride compound preferably contains a cyclic structure other than an anhydride ring structure (cyclic structure called non-dianhydride ring). In some preferred embodiments, the dianhydride compound is selected from, but is not limited to, one or a combination of more than two of compounds of pyromellitic dianhydride, benzophenonetetracarboxylic dianhydride, biphenyltetracarboxylic dianhydride, tetracarboxydiphthalic ether dianhydride, hexafluorotetracarboxylic dianhydride, triphenylbiether tetracarboxylic dianhydride, 1,2,4,5-cyclohexenetetracarboxylic dianhydride, cyclobutanetetracarboxylic dianhydride, bisphenol A type diether tetracarboxylic dianhydride, naphthalene-1,4,5,8-tetracarboxylic dianhydride, 3,4,9,10-perylenetetracarboxylic dianhydride, 3,3',4,4'-triphenylbiether tetracarboxylic dianhydride, and 1,2,3,4-cyclopentanetetracarboxylic dianhydride, further preferably one or two of pyromellitic dianhydride and cyclobutanetetracarboxylic dianhydride.

In the present disclosure, the epoxy compound used in the preparation of the stable dispersant may be any epoxide containing a double bond (olefinic double bond) capable of polymerizing with an olefinically unsaturated monomer, preferably a 1,2-epoxide. In some preferred embodiments, the epoxy compound is selected from, but is not limited to, one or a combination of more than two of glycidyl ether, glycidyl acrylate and derivatives thereof, preferably one or a combination of more than two of allyl glycidyl ether, glycidyl methacrylate, and glycidyl acrylate, and more preferably glycidyl methacrylate. There is no limit to the specific type of olefinically unsaturated monomers, for example, various olefinically unsaturated monomers that can be suitable for the preparation of copolymer polyols.

In some preferred embodiments, the molar ratio of the polyol, in particular polyether polyol, to the dianhydride compound is (0.2-4):1, preferably (1.5-2.5):1; and the molar ratio of the dianhydride compound to the epoxy compound is (0.1-2):1, preferably (0.3-8):1.

In the present disclosure, in the preparation of the stable dispersant, a catalyst may be used in step 2) to facilitate the reaction. The amount of the catalyst is preferably 0.01% (w/w) to 0.5% (w/w) of the mass of the polyol. Preferably, the catalyst is one or a combination of more than two of an organic phosphonic compound, an organic amine compound, and a tertiary amine. Further preferably, the organic phosphonic compound is selected from one or a combination of more than two of organic phosphorous halides and tetramethyl phosphine hydroxides, the organic amine compound is selected from at least one of imidazole or imidazole derivatives, and the tertiary amine is selected from one or a combination of more than two of triethylamine, diethylenetriamine, tripropylamine, and tributylamine. Still further preferably, the organic phosphorous halide is selected from one or a combination of more than two of a tetramethyl phosphine iodide, a tetramethyl phosphine bromide, a trimethyl benzyl phosphine bromide, a trimethyl benzyl phosphine chloride, an ethyl triphenyl phosphine iodide, an ethyltri(p-tolyl)phosphine bromide, and an ethyltri(p-tolyl) phosphine chloride.

In some preferred embodiments, in step 1), for the polyol, the number-average molecular weight is 2500 to 15000, preferably 5000 to 14000, and the average functionality is 2.0 or more, preferably 2.5 to 6.0.

The polyol used in the preparation of the stable dispersant is preferably a polyether polyol (often also called a polyoxyalkylene polyol). Such a polyether polyol is obtained by reacting a starter compound with an active hydrogen atom with one or more epoxy compounds, wherein the epoxy compounds are one or more of an ethylene oxide, a propylene oxide, and a butylene oxide.

The reactions in step 1) and step 2) are performed in the presence or absence of a solvent. Preferably, the solvent is a polar solvent free of protons, preferably the solvent is capable of dissolving the dianhydride compound and the epoxy compound, such as one or more of acetone, tetrahydrofuran, and methyl ethyl ketone.

In the present disclosure, in the preparation of the stable dispersant, the temperatures of the reactions in step 1) and step 2) are 60° C. to 150° C., more preferably 80° C. to 130° C., respectively. The reactions in step 1) and step 2) are performed at atmospheric pressure.

In the present disclosure, in the preparation of the stable dispersant, optionally, a polymerization inhibitor is further added in the reaction system of step 2) ("optionally" means that the polymerization inhibitor may or may not be added). For example, the polymerization inhibitor includes, but is not limited to, one or more of hydroquinone, p-t-butylcatechol, p-hydroxyanisole, methylhydroquinone, phenothiazine, and diphenylamine. The amount of the polymerization inhibitor is 0 to 1.5%, preferably 30 ppm to 2000 ppm of the total mass of the polyol.

Specifically, in some embodiments, the schematic diagram of the reaction for preparing the stable dispersant is shown in FIG. 1. In other embodiments, the schematic diagram of the reaction for preparing the stable dispersant is shown in FIG. 2. For ease of understanding, the structural schematic diagram of the stable dispersant obtained in some embodiments is shown in FIG. 7, and such a stable dispersant has dual active sites. The stable dispersant shown in FIG. 7 is the Gemini stable dispersant with dual polyether segments.

The stable dispersant provided by the present disclosure is particularly suitable for the application in preparing copolymer polyols. The preparation of copolymer polyols is well known in the art, and the copolymer polyols are obtained by polymerizing at least one olefinically unsaturated monomer and a base polyether polyol in the presence of a stable dispersant under the initiation of an initiator. Preferably, the reaction temperature is 80° C. to 150° C., more preferably 90° C. to 120° C., and the reaction pressure is 0 to 1 Mpa, preferably atmospheric pressure to 0.5 Mpa.

The base polyether polyol used in the preparation of copolymer polyols is selected according to the end use of the copolymer polyols and can be specifically selected by those skilled in the art as needed. For example, if the copolymer polyols are used in the production of block polyurethane foam, the polyether polyol for general-purpose polyurethane foam is selected to be used, which is a tri-functional base polyether polyol with a general hydroxyl value of 54 mgKOH/g to 58 mgKOH/g. If the copolymer polyols are used in the production of high resilient foam, the polyether polyol for high resilient foam is selected to be used, which is a high-activity tri-functional base polyether polyol with a general hydroxyl value of 33.5 mgKOH/g to 36.5 mgKOH/ g. Preferably, the base polyether polyol used in the present disclosure is a tri-functional polyether polyol with a hydroxyl value of 54 mgKOH/g to 58 mgKOH/g.

In some preferred embodiments, the amount of the olefinically unsaturated monomer is 20 wt % to 55 wt % of the total mass of the base polyether polyol, the olefinically unsaturated monomer, and the stable dispersant.

In some preferred embodiments, the amount of the stable dispersant is 0.3% to 10%, further preferably 2% to 5% of the total mass of the base polyether polyol and the olefinically unsaturated monomer.

The olefinically unsaturated monomer used in the preparation of the copolymer polyols in the present disclosure may use various olefinically unsaturated monomers allowed in the art, which is not specifically limited thereto. The olefinically unsaturated monomer includes, but is not limited to, one or more of conjugated aliphatic dienes, vinyl aromatic compounds, $\alpha,\beta$-olefinically unsaturated nitriles, $\alpha,\beta$-olefinically unsaturated nitrile amides, $\alpha,\beta$-olefinically unsaturated carboxylic acids, $\alpha,\beta$-olefinically unsaturated carboxylic esters, vinyl esters, vinyl ethers, vinyl ketones, vinyl halides, and vinylidene halides, preferably vinyl aromatic compounds and $\alpha,\beta$-olefinically unsaturated nitriles. More preferably, the olefinically unsaturated monomer is one or two of styrene and acrylonitrile, and the molar ratio of styrene to acrylonitrile is preferably 50:50 to 100:0.

In the preparation of the copolymer polyols, the polymerization of the olefinically unsaturated monomer is performed under the initiation of the initiator. In some preferred embodiments, the amount of the initiator is 0.01 wt % to 5 wt % of the total mass of the base polyether polyol and the olefinically unsaturated monomer. The specific type of the initiator is not particularly limited, and the initiator may be any polymerization initiator commonly used in the art. For example, the initiator is selected from one or a combination of more than two of peroxides and azo compounds. The peroxides, for example, include one or more of dibenzoyl peroxide, lauroyl peroxide, tert-butyl hydroperoxide, benzoyl peroxide, and di-tert-butyl peroxide. The azo compounds, for example, include one or more of azobisisobutyronitrile (AIBN), azoisovaleronitrile (AMBN), and dimethyl azobisisobutyrate (V601).

In the present disclosure, the polymerization of the olefinically unsaturated monomer is preferably performed in the presence of a chain-transfer agent. The amount of the chain-transfer agent is 0.1 wt % to 6 wt %, further preferably 0.2 wt % to 5 wt % of the total mass of the base polyether polyol and the olefinically unsaturated monomer. The specific type of the chain-transfer agent is not particularly limited, and the chain-transfer agent, for example, is one or more of 1-butanol, 2-butanol, isopropanol, ethanol, methanol, water, cyclohexane, and thiol, such as one or more of dodecanethiol, ethanethiol, 1-heptanethiol, 2-octanethiol, and toluenethiol.

Other compounds may also be used as needed in the process for preparing the copolymer polyols, such as compounds that promote the mixing of components, compounds that have a viscosity reducing effect, and/or compounds that can enable one or more of the components used to better dissolved in the reaction medium. The compound having a viscosity reducing effect and thus enabling the components to be better mixed, for example, is one or more of toluene or dichloromethane.

In the present disclosure, the process for preparing the copolymer polyols may be carried out in an intermittent or continuous operation. After the preparation of the copolymer polyols, the copolymer polyols generally need to be subjected to the removal process of unreacted monomer and the chain transfer agent, which is well known in the art. Common removal means in the art include chemical unit operations such as distillation, flash evaporation, scraper, or thin-film evaporation, which will not be described in detail herein.

The copolymer polyols provided by the present disclosure are suitable for the synthesis of polyurethane foam materials. The polyurethane foam materials can foam a composition including the copolymer polyols obtained by the preparation method described above and polyisocyanates to obtain flexible polyurethane foams. The process for preparing polyurethane foams is known in the art. In the foaming system of copolymer polyols and polyisocyanates, polyurethane catalysts, crosslinking agents, foaming agents, foam stabilizers, auxiliaries, and the like may be added as needed.

In the preparation of the copolymer polyols, in some embodiments, the polyurethane catalyst used is, for example, an organometallic compound such as stannous octoate, stannous oleate, dibutyltin dilaurate, dibutyltin acetate, and dibutyltin diacetate; or the polyurethane catalyst is, for example, an organic amine catalyst such as bis(2,2'-dimethylamino)ethyl ether, trimethylamine, triethylamine, triethylenediamine, and dimethylethanolamine. In the preparation of the copolymer polyols, the foaming agent used include, for example, water, acetone, carbon dioxide, halogenated hydrocarbons, aliphatic alkanes, alicyclic alkanes, and the like. The suitable crosslinking agent is, for example, diethanolamine (DEOA) and the like. The suitable foam stabilizer is, for example, an organopolysiloxane surfactant and the like. In addition, the auxiliaries, such as flame retardants, fillers, light stabilizers, and antioxidants, are usually used in the process of preparing polyurethane foams.

The technical solutions provided by the present disclosure have the following beneficial effects.

The stable dispersant prepared according to the present disclosure does not need to be refined or separated and can be used directly in subsequent reactions. The process for preparing the stable dispersant in the present disclosure is an atmospheric reaction and does not involve the use of EO capping. In addition, the viscosity of the prepared stable dispersant is low, and in the preparation of the copolymer polyols, the operation of mixing the stable dispersant with the material(s) in the polymerization reaction system is simple and convenient. Meanwhile, because the stable dispersant provided by the present disclosure contains many active sites, the synthesized copolymer polyols have great stable dispersity, and thus the prepared copolymer polyols can obtain a relatively single particle size. The prepared copolymer polyols, when applied to downstream foam articles, can make the downstream foam articles obtain excellent cell-opening performance and foam homogenizing property.

DETAILED DESCRIPTION

Figure 1:
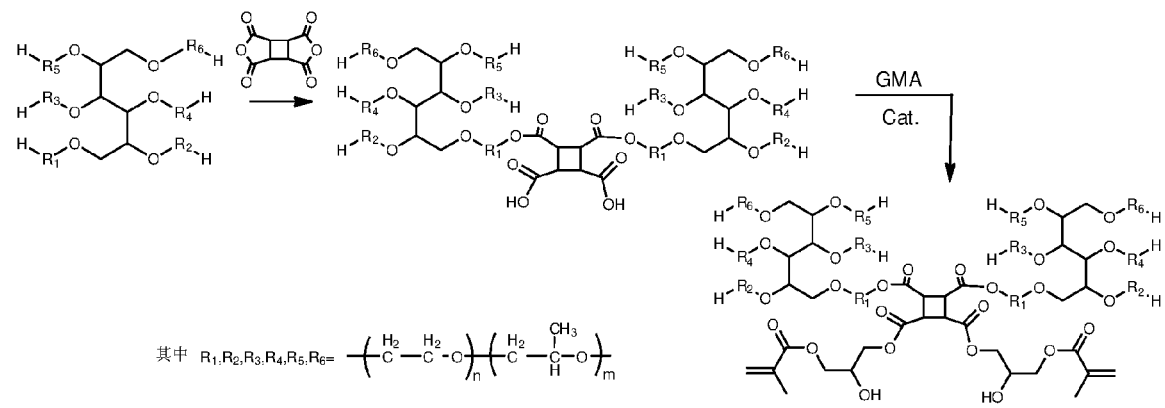
FIG. 1 is a schematic diagram of the reaction for preparing a stable dispersant in one embodiment.

For a better understanding of the technical solutions of the present disclosure, the content of the present disclosure will be further described below in conjunction with the following examples, but is not limited to the following examples.

The detection methods involved in the following examples and comparative example are described below.

Hydroxyl number: GB 12008.3-2009 Plastics-Polyether Polyols-Part 3: Determination of hydroxyl number.

Viscosity: GB 12008.7-2010 Plastics-Polyether Polyols-Part 7: Determination of viscosity.

Degree of unsaturation: GB 12008.6-2010 Plastics-Polyether polyols-Part 6: Determination of degree of unsaturation.

Solid content: GB/T 31062-2014 Polymeric Polyols.

Unless otherwise specified, the reactions in the following examples were all performed at atmospheric pressure, and the processes involved in the reactions were all performed under nitrogen.

Polyether polyol A: in the conditions that sorbitol was used as a starter, the concentration of the catalyst (KOH) was 0.3 wt % (w/w) of the mass of propylene oxide (PO), the reaction temperature was controlled to be about 110±5° C., and the pressure was lower than 0.15 MPa, the reaction was carried out, and after PO was fed, PO was aged, and the reaction continued for 2 hours and the degasification was carried out for 1 hour. After the degasification, ethylene oxide (EO) was fed, and with the reaction temperature controlled at about 110±5° C., the reaction was carried out at a pressure lower than 0.15 MPa. After the material feeding was completed, the material was aged, and the reaction was continued for 2 hours and the degasification was carried out for 1 hour. At this time, the reaction stage ended. With the temperature controlled at 85° C. to 90° C., soft water and phosphoric acid were added to neutralize the reaction product, and the neutralization product was dehydrated, filtered, and cooled to obtain the ejection. In the above process, the mass ratio of sorbitol/EO/PO was 1.08/4.95/93.97, the hydroxyl number was about 28 mgKOH/g, and the number-average molecular weight determined by GPC was 12001.

Polyether polyol B: in the conditions that trimethylolpropane was used as a starter, the concentration of the catalyst (KOH) was 0.3 wt % (w/w) of the mass of propylene oxide (PO), the reaction temperature was controlled to be about 110±5° C., and the pressure was lower than 0.15 MPa, the reaction was carried out, and after PO was fed, PO was aged, and the reaction continued for 2 hours and the degasification was carried out for 1 hour. After the degasification, ethylene oxide (EO) was fed, and with the reaction temperature controlled at about 110±5° C., the reaction was carried out at a pressure lower than 0.15 MPa. After the material feeding was completed, the material was aged, and the reaction was continued for 2 hours and the degasification was carried out for 1 hour. At this time, the reaction stage ended. With the temperature to be controlled at 85° C. to 90° C., soft water and phosphoric acid were added to neutralize the reaction product, and the neutralization product was dehydrated, filtered, and cooled to obtain the ejection. In the above process, the mass ratio of trimethylolpropane/EO/PO was 1.91/9.81/88.26, the hydroxyl number was about 24 mgKOH/g, the viscosity was 858 cp (25° C.), and the number-average molecular weight determined by GPC was 7003.

Base polyol C: conventional polyether polyol for soft foam, which was prepared by reacting glycerol with propylene oxide and ethylene oxide, available from Wanhua Chemical Group Co., Ltd., Brand No.: WANOL®F3156.

Comparative stabilizer: 3000 g of polyether polyol B and 30.6 g of maleic anhydride were heated to 120° C., and then reacted under the protection of nitrogen for 12 hours. 50 g of ethylene oxide (EO) was then added, and the reaction continued for 4 hours. Unreacted EO was removed to obtain a product which was a transparent brown-yellow liquid with a viscosity of 4100 cp (25° C.) and an unsaturation degree of 0.032 meq/g.

OA-12: dimethyldodecyl tertiary amine was oxidized, dehydrated, and dried to obtain a viscous liquid.

WANNATE®8001: modified MDI (diphenylmethane diisocyanate), from Wanhua Chemical Group Co., Ltd.

BiCAT®8106: organic bismuth catalyst, from the Shepherd Chemical Company.

B-8715LF2: foam Stabilizer, from TMG Chemicals Co., Ltd.

Other raw materials involved in the following examples were purchased from Aladdin Biochemical Technology Co., Ltd without otherwise specified.

Example 1

Preparation of Stable Dispersant 1 (refer to FIG. 1 for the schematic diagram of the reaction) 3000 g of polyether polyol A, 40.3 g of cyclobutanetetracarboxylic dianhydride, and 180 g of acetone were mixed homogeneously, heated to 100° C., and stirred and refluxed for 16 hours. 3.1 g of ethyl triphenyl phosphine iodide was added and stirred to dissolve, and then 40.3 g of glycidyl methacrylate (GMA) and 1.78 g of hydroquinone were added and reacted at 120° C. overnight. The obtained product was a transparent light-yellow liquid with a viscosity of 2580 mPa·s and an unsaturation degree of 0.076 meq/g. The obtained product was higher than the comparative stabilizer in terms of unsaturation degree, indicating that the obtained product had more active sites.

Example 2

Figure 2:
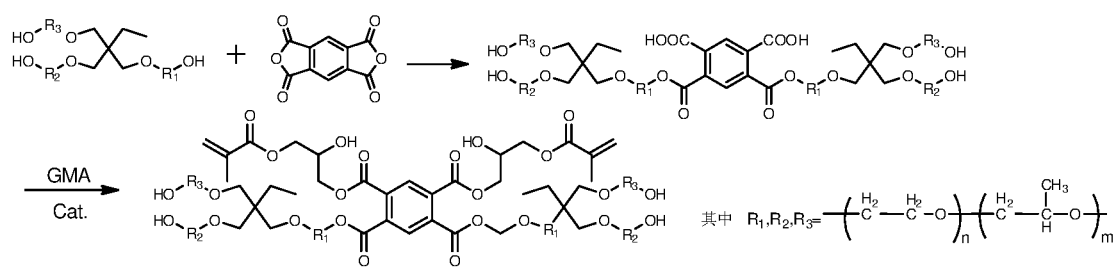
FIG. 2 is a schematic diagram of the reaction for preparing a stable dispersant in another embodiment.

Preparation of Stable Dispersant 2 (refer to FIG. 2 for the schematic diagram of the reaction, in which the epoxy compound used was glycidyl methacrylate (GMA)) 3000 g of polyether polyol B and 41.9 g of pyromellitic dianhydride were mixed homogeneously, heated to 120° C., and then reacted under the protection of nitrogen for 18 hours. 3.0 g of ethyl triphenyl phosphine iodide (ETPPI) was added and stirred to dissolve, and then 36.1 g of glycidyl acrylate (GA) and 0.90 g of hydroquinone were added and reacted at 120° C. overnight. The obtained product was a transparent light-yellow liquid with a viscosity of 1780 mPa·s and an unsaturation degree of 0.092 meq/g. The obtained product was higher than the comparative stabilizer in terms of unsaturation degree, indicating that the obtained product had more active sites.

Example 3

Preparation of Copolymer Polyol 1

A four-necked bottle of 500 ml provided with a stirrer, a heating device, a temperature control device, and a feeder was used as the reactor. 55.4 g of base polyether polyol (from Wanhua, Brand No.: WANOL®3156) and 3.6 g of the stable dispersant 1 were added to the reactor. After nitrogen replacement, the mixture was stirred and slowly heated to 110° C., a top material (a mixed liquid of 10.47 g of isopropanol, 85.71 g of base polyether polyol WANOL®3156, 46.55 g of acrylonitrile, 69.83 g of styrene, and 1.21 g of azobisisobutyronitrile) was continuously added, and the temperature was controlled to be 115° C. to 120° C. The mixed liquid was added dropwise within 100 minutes. Once the material feeding was completed, the reaction was aged for 1 hour and heated to 160° C. The unreacted monomer was removed under vacuum for 2 hours to obtain the product. Then the product index was measured. Residual styrene/acrylonitrile/isopropanol was 2/2/4 ppm, the hydroxyl number was 29.8 mgKOH/g, the solid content was 44.9%, and the viscosity was 5329 cp (25° C.).

Example 4

Preparation of Copolymer Polyol 2

A four-necked bottle of 500 ml provided with a stirrer, a heating device, a temperature control device, and a feeder was used as the reactor. 55.4 g of base polyether polyol (from Wanhua, Brand No.: WANOL®3156) and 3.4 g of the stable dispersant 2 were added to the reactor. After nitrogen replacement, the mixture was stirred and slowly heated to 110° C., a top material (a mixed liquid of 10.47 g of isopropanol, 85.71 g of base polyether polyol WANOL®3156, 46.55 g of acrylonitrile, 69.83 g of styrene, and 1.21 g of azobisisobutyronitrile) was continuously added, and the temperature was controlled to be 115° C. to 120° C. The mixed liquid was added dropwise within 100 minutes. Once the material feeding was completed, the reaction was aged for 1 hour. The unreacted monomer was removed under vacuum for 2 hours to obtain the product. Then the product index was measured. Residual styrene/acrylonitrile/isopropanol was 2/1/3 ppm, the hydroxyl number was 30.4 mgKOH/g, the solid content was 44.8%, and the viscosity was 5698 cp (25° C.).

COMPARATIVE EXAMPLE

A four-necked bottle of 500 ml provided with a stirrer, a heating device, a temperature control device, and a feeder was used as the reactor. 55.4 g of base polyether polyol (from Wanhua, Brand No.: WANOL®3156) and 5.6 g of the comparative stabilizer were added to the reactor. After nitrogen replacement, the mixture was stirred and slowly heated to 110° C., a top material (a mixed liquid of 10.47 g of isopropanol, 85.71 g of base polyether polyol WANOL®3156, 46.55 g of acrylonitrile, 69.83 g of styrene, and 1.21 g of azobisisobutyronitrile) was continuously added, and the temperature was controlled to be 115° C. to 120° C. The mixed liquid was added dropwise within 100 minutes. Once the material feeding was completed, the reaction was aged for 1 hour. The unreacted monomer was removed under vacuum for 2 hours to obtain the product.

Then the product index was measured. Residual styrene/acrylonitrile/isopropanol was 2/3/6 ppm, the hydroxyl number was 29.2 mgKOH/g, the solid content was 45.0%, and the viscosity was 5783 cp (25° C.). Compared with Examples 3-4, the viscosity of the copolymer polyol obtained in the Comparative Example is much higher when the stabilizer is used in a higher amount.

Example 5

Figure 3:
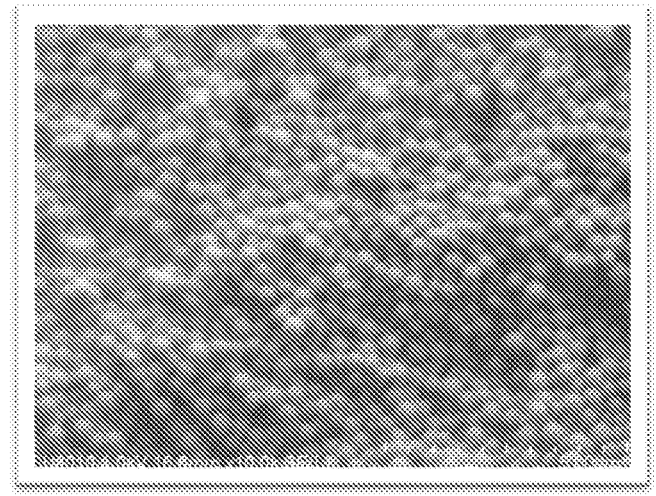
FIG. 3 is a diagram showing the SEM detection result of the copolymer polyol obtained in Example 3.
Figure 4:
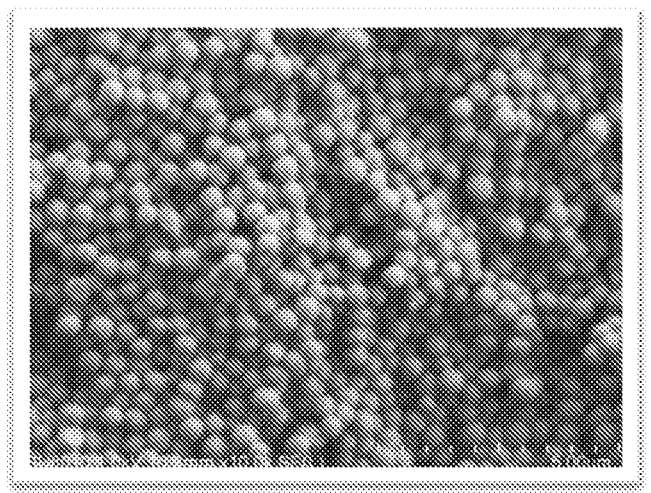
FIG. 4 is a diagram showing the SEM detection result of the copolymer polyol obtained in Example 4.
Figure 5:
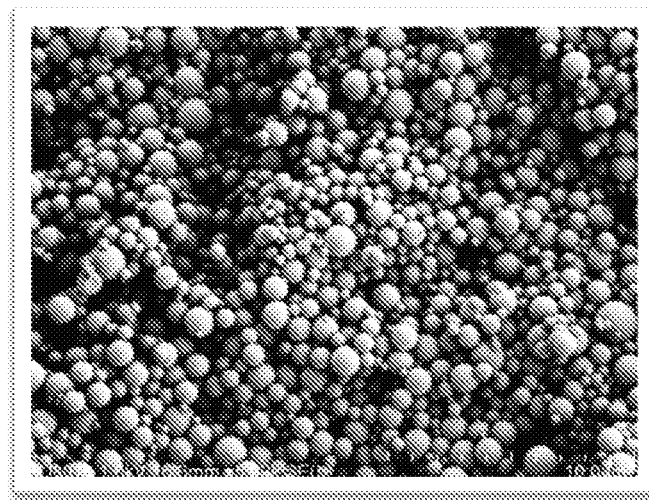
FIG. 5 is a diagram showing the SEM detection result of the copolymer polyol obtained in Comparative Example.
Figure 6:
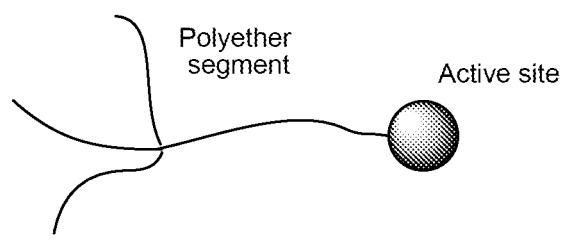
FIG. 6 is a structural schematic diagram of the stabilizer in the existing art.
Figure 7:
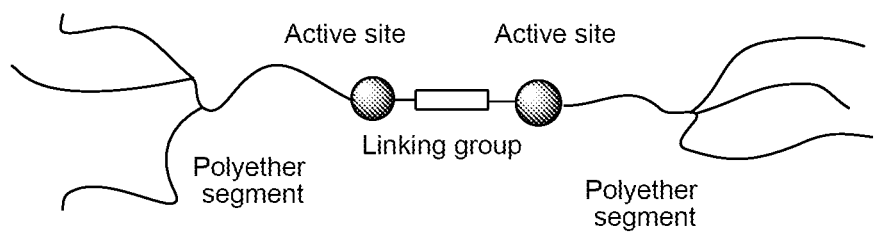
FIG. 7 is a structural schematic diagram of the stable dispersant obtained in some embodiments.

The copolymer polyols prepared in Examples 3 and 4 and Comparative Example were washed with ethanol and then centrifuged. The solids were collected and tested by SEM. The results of Examples 3 and 4 are shown in FIGS. 3 and 4, respectively, and the result of Comparative Example is shown in FIG. 5. It can be seen that the copolymer polyols prepared according to the present disclosure were homogeneous in particle size, fine in appearance, and showed no agglomeration.

Example 6

Method for Preparing Polyurethane Foams

The experiments 1#, 2#, and 3# were carried out according to the raw materials and parts by weight thereof shown in Table 1 to prepare combined materials. The combined material in each experiment and the isocyanate raw material were placed at a constant temperature of 22° C. for 3 hours. 100 g of each combined material was mixed with 60 g of WANOL®8001 component in a stirrer (rotational speed: 3000 rpm) for 6 seconds. The stirred mixture was then quickly poured into an aluminum open mold (size: 300 mm length, 300 mm width, and 50 mm thickness) previously heated to 60° C. to allow the mixture to foam. After 7 minutes, the foams were taken out from the mold to obtain polyurethane foams.

TABLE 1

Combined material formulation (parts by weight)

| Material | 1# | 2# | 3# |
|---|---|---|---|
| Polymer dispersion amount | 33.70 | 33.70 | 33.70 |
| WANOL ®F3156 (polyether polyol) | 59.46 | 59.46 | 59.46 |
| Diethanolamine | 0.50 | 0.50 | 0.50 |
| Water | 4.16 | 4.16 | 4.16 |
| N,N-bis(dimethylaminopropyl)isopropanolamine | 0.40 | 0.40 | 0.40 |
| N,N,N'-trimethyl-N'-hydroxyethylbisaminoethylether | 0.50 | 0.50 | 0.50 |
| BiCAT 8106 (organic bismuth catalyst) | 0.10 | 0.10 | 0.10 |
| B-8715 LF2 (foam stabilizer) | 1.19 | 1.19 | 1.19 |

The polymer dispersion used in experiment 1# was the copolymer polyol prepared in Comparative Example, and the polymer dispersions used in experiments 2# and 3# were the copolymer polyols prepared in Examples 3 and 4, respectively.

The performance indices and corresponding test criteria for testing the prepared polyurethane foams are shown in Table 2.

TABLE 2

Polyurethane foam performances

| Test item | Test criteria | 1# | 2# | 3# |
|---|---|---|---|---|
| VOC | VDA 278 90° C./0.5 h | 65 | 50 | 50 |
| Smell, µgC/g | VDA 270B3 80° C./2 h | 5 | 3 | 2 |

TABLE 2-continued

Polyurethane foam performances

| Test item | Test criteria | 1# | 2# | 3# |
|---|---|---|---|---|
| Tensile strength, Kpa | ISO1798 | 90 | 100 | 105 |
| Elongation at break, Kpa | ISO1798 | 75 | 80 | 85 |

From the experimental results of Table 2, it can be seen that the copolymer polyols prepared using the novel stabilizer performed better in tensile strength and elongation at break.

Those skilled in the art will appreciate that numerous modifications or adaptations may be made to the present disclosure based on the technical teachings of the present description. These modifications or adaptations shall be within the scope of the present disclosure as defined by the claims.

What is claimed is:

1. A preparation method for a stable dispersant, comprising:
    1) Contacting a polyol with a dianhydride compound for reaction to prepare an adduct; and
    2) performing a ring-opening addition reaction on the adduct obtained in step 1) and an epoxy compound to prepare a stable dispersant;
    wherein the dianhydride compound does not contain a double bond that may copolymerize with an olefinically unsaturated monomer while the epoxy compound contains a double bond that may copolymerize with an olefinically unsaturated monomer, and the polyol is a polyester polyol and/or a polyether polyol.

2. The preparation method according to claim 1, wherein the dianhydride compound is one selected from the group consisting of pyromellitic dianhydride, benzophenonetetracarboxylic dianhydride, biphenyltetracarboxylic dianhydride, tetracarboxydiphthalic ether dianhydride, hexafluorotetracarboxylic dianhydride, triphenylbiether tetracarboxylic dianhydride, 1,2,4,5-cyclohexenetetracarboxylic dianhydride, cyclobutanetetracarboxylic dianhydride, bisphenol A type diether tetracarboxylic dianhydride, naphthalene-1,4,5,8-tetracarboxylic dianhydride, 3,4,9,10-perylenetetracarboxylic dianhydride, 3,3',4,4'-triphenylbiether tetracarboxylic dianhydride, 1,2,3,4-cyclopentanetetracarboxylic dianhydride, and a combination of more than two selected therefrom.

3. The preparation method according to claim 2, wherein the epoxy compound is one selected from the group consisting of glycidyl ether, glycidyl acrylate, derivatives thereof, and a combination of more than two selected therefrom.

4. The method according to claim 1, wherein the molar ratio of the polyol to the dianhydride compound is (0.2-4):1; and wherein the molar ratio of the dianhydride compound to the epoxy compound is (0.1-2): 1.

5. The preparation method according to claim 1, wherein the molar ratio of the dianhydride compound to the epoxy compound is (0.3-8): 1.

6. The preparation method according to claim 1, wherein in step 1), for the polyol, the number-average molecular weight is 2500 to 15000, and the average functionality is 2.0 or more.

7. The preparation method according to claim 1, wherein the temperatures of the reactions in step 1) and step 2) are 60° C. to 150° C.

* * * * *